United States Patent
Hendriks et al.

(10) Patent No.: US 10,299,684 B2
(45) Date of Patent: May 28, 2019

(54) USER INTERFACE FOR PHOTONIC TOOLS AND ELECTROMAGNETIC TRACKING GUIDED BRONCHOSCOPE

(71) Applicant: KONINKLIJKE PHILIPS N.V., Eindhoven (NL)

(72) Inventors: Bernardus Hendrikus Wilhelmus Hendriks, Eindhoven (NL); Torre Michelle Bydlon, Eindhoven (NL); Arnoldus Theodorus Martinus Hendricus Van Keersop, Eindhoven (NL); Gerhardus Wilhelmus Lucassen, Eindhoven (NL); Vijay Parthasarathy, Andover, MA (US); Vishnu Vardhan Pully, Eindhoven (NL); Marjolein Van Der Voort, Eindhoven (NL); Manfred Mueller, Eindhoven (NL); Gerardus Henricus Maria Gijsbers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 179 days.

(21) Appl. No.: 15/105,892

(22) PCT Filed: Dec. 17, 2014

(86) PCT No.: PCT/EP2014/078102
§ 371 (c)(1),
(2) Date: Jun. 17, 2016

(87) PCT Pub. No.: WO2015/091580
PCT Pub. Date: Jun. 25, 2015

(65) Prior Publication Data
US 2016/0317035 A1 Nov. 3, 2016

Related U.S. Application Data

(60) Provisional application No. 61/918,936, filed on Dec. 20, 2013.

(30) Foreign Application Priority Data

Jan. 22, 2014 (EP) .................................... 14152052

(51) Int. Cl.
*A61B 5/00* (2006.01)
*A61B 1/267* (2006.01)
(Continued)

(52) U.S. Cl.
CPC .......... *A61B 5/0075* (2013.01); *A61B 1/2676* (2013.01); *A61B 5/0084* (2013.01);
(Continued)

(58) Field of Classification Search
USPC .......................................... 600/476; 382/131
See application file for complete search history.

(56) References Cited

U.S. PATENT DOCUMENTS

| | | | |
|---|---|---|---|
| 2009/0113295 A1 | 4/2009 | Halpern | |
| 2012/0087562 A1* | 4/2012 | Isaacs | G06F 19/321 382/131 |

(Continued)

FOREIGN PATENT DOCUMENTS

| | | |
|---|---|---|
| WO | 2009109879 A2 | 9/2009 |
| WO | 2010085348 A1 | 7/2010 |
| WO | 2013144841 A2 | 10/2013 |

OTHER PUBLICATIONS

N. Moayeri, et al, Differences in quantitative architecture of sciatic nerve may explain differences in potential vulnerability to nerve injury, onset time, and minimum effective anesthetic volume, Anesthesiology vol. 111 (2009) p. 1128-1134.

(Continued)

*Primary Examiner* — Nicole F Lavert
*Assistant Examiner* — Nicole F Johnson

(57) ABSTRACT

A system and method to support exploring the interior of an object. The system 100, 200 includes a graphical user (Continued)

interface generator (GG) to generate a graphical user interface (GUI). The graphical user interface (GUI) includes an indicator (NC) of a current position of an interventional tool (IT) inside an object (OB). There is also an exploratory indictor (PC) to indicate material composition and/or type that surrounds the tool's tip (TP) at a current position in the object (OB). The exploratory indicator (PC) includes a pointer element for a current reading against a dial element for a range of possible values.

18 Claims, 14 Drawing Sheets

(51) Int. Cl.
  A61B 5/06 (2006.01)
  A61B 34/00 (2016.01)
  A61B 90/00 (2016.01)
  A61B 10/02 (2006.01)
  A61B 17/00 (2006.01)
  A61B 34/20 (2016.01)
  A61B 8/08 (2006.01)

(52) U.S. Cl.
  CPC .............. A61B 5/064 (2013.01); A61B 5/742 (2013.01); A61B 10/0233 (2013.01); A61B 34/25 (2016.02); A61B 90/37 (2016.02); A61B 8/0841 (2013.01); A61B 2017/00061 (2013.01); A61B 2034/2051 (2016.02); A61B 2034/2063 (2016.02); A61B 2090/365 (2016.02); A61B 2090/373 (2016.02); A61B 2090/378 (2016.02); A61B 2090/3764 (2016.02)

(56) References Cited

U.S. PATENT DOCUMENTS

2014/0275986 A1* 9/2014 Vertikov ................ A61B 5/061
    600/424
2014/0276108 A1* 9/2014 Vertikov .............. A61B 5/0084
    600/478

OTHER PUBLICATIONS

T.J. Farrel, et al, "A diffusion theory model of spatially resolved, steady-state diffuse reflectance for the non-invasive determination of tissue optical properties," Med. Phys. 19 (1992) p. 879-888.

R. Nachabé, et al, "Estimation of biological chromophores using diffuse optical spectroscopy : benefit of extending the UV-VIS wavelength range to include 1000 to 1600 nm," Optics Express, vol. 18, 2010, pp. 879-888.

R. Nachabe et al, "Estimation of lipid and water concentrations in scattering media with diffuse optical spectroscopy from 900 to 1600 nm," Journal of Biomedical Optics, vol. 15, May 2010, pp. 037015-10.

M. Müller et al, "Recovering intrinsic fluorescence by Monte Carlo modeling", J. Biomed. Optics vol. 18 (2013) p. 027009-1 to 027009-13.

R. Nachabé, et al, Diagnosis of breast cancer using optical spectroscopy from 500 to 1600 nm: a comparison of classification methods, J. Biomed. Opt. 16 (2011) p. 087010.

D. Evers et al, "Diffuse reflectance spectroscopy: A new guidance tool for improvement of biopsy procedures in lung malignancies", Clinical Lung Cancer vol. 13 (2012) pp. 424-431.

J. Spliethoff et al, "Improved identification of peripheral lung tumors by using diffuse reflectance and fluorescence Spectroscopy", Lung Cancer 80 (2013) p. 165-171.

* cited by examiner

US 10,299,684 B2

USER INTERFACE FOR PHOTONIC TOOLS AND ELECTROMAGNETIC TRACKING GUIDED BRONCHOSCOPE

CROSS-REFERENCE TO PRIOR APPLICATIONS

This application is the U.S. National Phase application under 35 U.S.C. § 371 of International Application No. PCT/EP2014/078102, filed on Dec. 17, 2014, which claims the benefit of U.S. Provisional Patent Application No. 61/918,936, filed on Dec. 20, 2013 and European Patent Application No. 14152052.8, filed on Jan. 22, 2014. These applications are hereby incorporated by reference herein.

FIELD OF THE INVENTION

The invention relates to a system for exploration of the interior of an object, to a method of supporting exploring the interior of an object, to a computer program element, and to a computer readable medium.

BACKGROUND OF THE INVENTION

Minimally invasive techniques have become the mainstay of modern medical practice. A host of sophisticated technologies and associated tools have been developed proposed in the past to help the interventionalist to make internals of the patient relatively easily accessible. Yet, with all those tools at the disposal in modern cath labs (catheterization laboratories), quickly finding one's way around inside the patient and to identify with great certainty the desired target site still remains challenging. Examples of interventional procedures are bronchoscopy or regional/local anesthetic administration.

SUMMARY OF THE INVENTION

There may therefore be a need for alternative methods and systems to support interventional procedures.

The object of the present invention is solved by the subject matter of the independent claims where further embodiments are incorporated in the dependent claims. It should be noted that the following described aspect of the invention equally apply to the method of supporting exploring the interior of an object, to the computer program element and to the computer readable medium.

According to a first aspect of the invention there is provided a system for exploration of the interior of an object, comprising:

an interventional tool having a tip portion for introduction into the object;

navigation equipment configured to produce current positional information indicative of a current position of the tip inside the object whilst the tool resides in the object;

a probe for introduction into the object, configured to receive non-ionizing radiation reflected off the interior of the object;

a spectral analyzer (SA) configured to spectrally analyze the received radiation into exploratory information about material or composition and/or tissue structure of the object's interior at or around the current tip position of the interventional tool, the exploratory information comprising at least one measurement value for a material type present at or around the current tip position of the interventional tool and/or a scattering measurement value for an amount of scattering as per the received radiation;

a graphical user interface generator (GG) configured to produce a graphics display (GUI) on a display unit including, when displayed:

i) at least one exploratory information indicator for the scatter measurement value or for the material type measurement value or for a value derived from either or both of said measurement values, the exploratory information indicator comprising a) a pointer element configured to indicate a current reading of the measurement value or a current reading of the derived value and b) a dial element configured to indicate a range of values, with the pointer element being displayed against the dial element; and ii) a position indicator for the current positional information of the tip's position in the object's interior.

The system further comprises the display unit (MT) for displaying the graphics display (GUI) when the system is use.

In other words, the GUI as proposed herein allows a view in a "dashboard" like appearance" on what type of tissue can found at the current tool position. "Material" as used herein includes in particular (but not only) chromophores (that is, substances that at least partially absorb light) but also includes "pure scatterers", that is, substances that do not absorb light.

According to one embodiment, the spectral analyzer is configured to discriminate the material measurement value into amounts of any one of a first material type and a second material type, wherein the graphics display (GUI) generated by the graphical user interface generator (GG) includes three discrete exploratory information indicators, each dedicated to the amounts of the two material types and the scattering value, respectively.

According to one embodiment, the spectral analyzer is configured to discriminate the material measurement value into amounts of any one of a first material type and a second material type, wherein the spectral analyzer (SA) is configured to combine the scattering value and the measured amounts for the two material types into a single super value, wherein the least one exploratory information indicator is for indicating said single super value.

According to one embodiment, the derived value is a probability value that relates to the probability of the first tissue type being in one of at least two states. For instance, in one embodiment, the probability relates to tissue malignancy.

According to one embodiment, the first or second material measurement value relates to the amount or density or concentration of the first or second material currently present at or around the tip of the interventional tool.

According to one embodiment, the exploratory information indicator includes a graphical indication for two probability densities. One probability density describes the distribution of the measurement value for a first material type and the other probability density describes the distribution of the measured value for a second material type. The exploratory information indicator thereby supports exploring transitions of strata of the two material types within the object. The graphical indication of at least one of the two probability densities is by curve representation or by color-coding.

According to one embodiment, the navigation equipment is an electromagnetic tracking device with a sensor attached to the interventional tool to relate its tip position to an electromagnetic field strength sensed by the sensor and wherein the position indicator is a graphical symbol superimposed on imagery of the object's interior. In other embodiments, the navigation equipment comprises a fluoroscopy imaging device or an ultrasound imaging device or X-ray or CT or MRI or PET-CT. The positional indicator is then defined by the footprint of the tip of the interventional tool in a current fluorogram or in an ultrasound image, respectively.

According to one embodiment, the first or second material is hemoglobin or water and the respective measurement value relates to a respective concentration of hemoglobin or water. It has been observed, that the "triade" of water and blood and scattering together affords a good detection rate of malignant tissue in particular for lung tissue.

According to one embodiment, the dial element is graduated and/or color- or grey-value coded to support easier read-off According to one embodiment, a position of the pointer relative to the dial changes responsive to a change of position of the interventional tool within the object.

According to one embodiment, the tool comprises an endoscope and/or a catheter and/or a biopsy needle and or a forceps biopsy tool and/or a brush biopsy tool and/or a needle for fluid injection into the object. Any tool that can be used in a working channel of an endoscope is envisaged herein.

According to one embodiment, the system is configured so that, responsive to the spectral analyzer's analyzing the received radiation into the current material type measurement value or into the scatter measurement value, the graphical user interface generator operates to include in the graphics display a measurement marker whose position in the graphics display corresponds to the current positional information. The measurement marker is color- and/or grey-value and/or shape coded according to the current material or material type measurement value or the scatter measurement value. This allows gradually building up a visually the distribution of the various material types in the region measured by the probe. Also, users may easier "back-track" their measurement sites and then compare the values as per their color- and/or grey-value and/or shape coding. The system thereby supports users in their decision on where to perform an action, for instance where to biopsy etc. In yet other words, measurement markers allow visually position and value of the measurement values. The markers are shown in one embodiments overlaid at the corresponding position in one or more respective copies (one for each material and or tissue type) of imagery of the object's interior.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
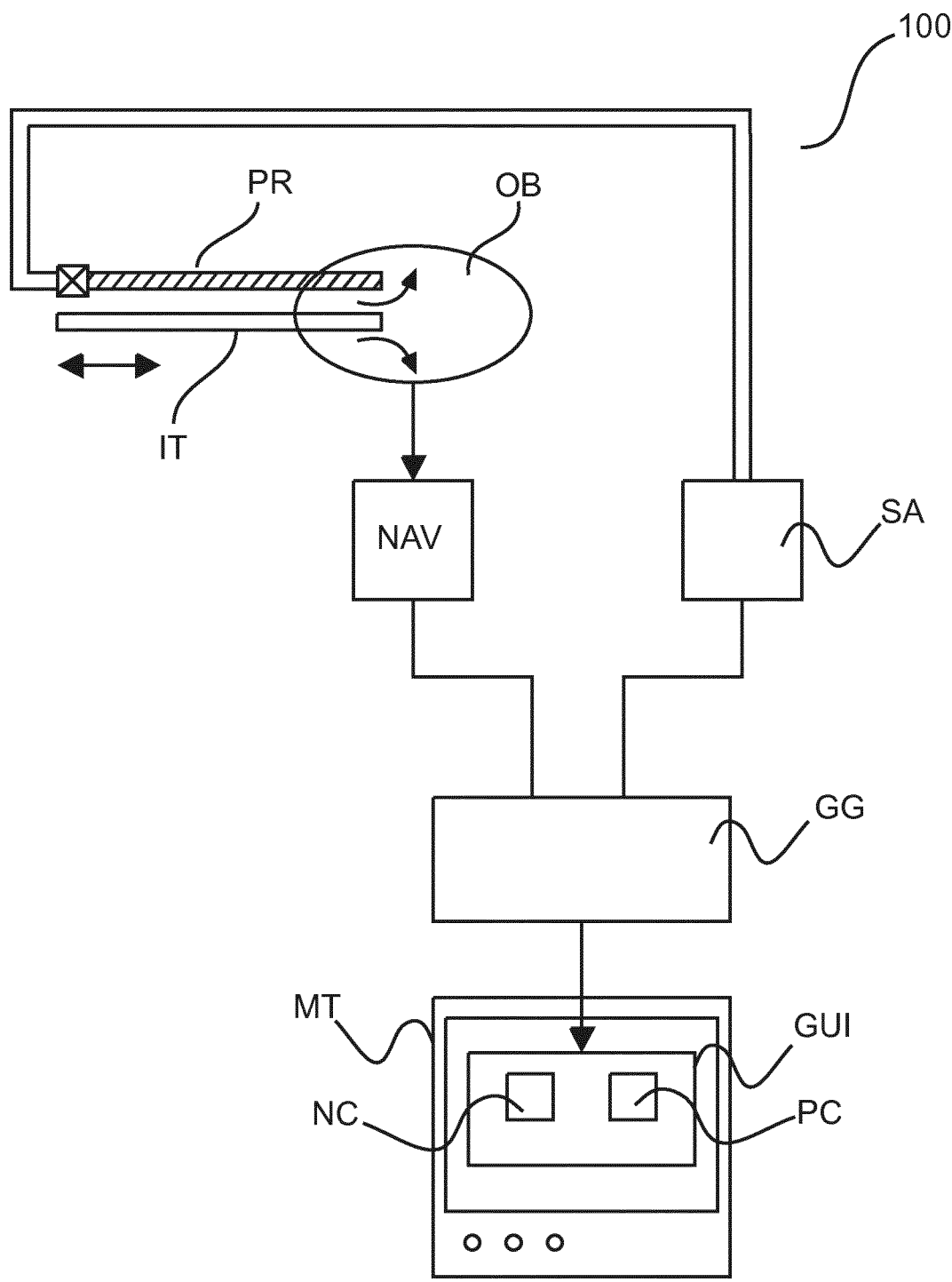
FIG. 1 shows a schematic block diagram of a system for exploring the interior of an object.

With reference to FIG. 1 there is shown a system 100 for supporting exploration of the interiors of an object OB. The object may be a patient or animal body or any specific organ therein. The system 100 includes a probe PR for introduction into the object. There is also an interventional tool IT for taking samples from identified tissue or to performing other tasks within the object at a required or desired site therein. The probe PR and the interventional tool IT may be formed as a unitary combo-tool. The probe and/or tool is coupled by a suitable communication means such as optical waveguides (shown as double lines in FIG. 1) to a spectral analyzer SA. There is also a navigation component NAV that is preferably based on live or pre-interventional imagery of the object.

Navigation information produced by navigation component NAV and exploratory information gathered by the spectral analyzer about the internals of the object (for example type of tissue or material/chromophore composition that is present around the tip portion of the interventional tool at a current position within the object) are fed into a graphical user interface generated GG.

Graphical user interface generator GG includes suitable back end circuitry to control a video card of a computer system connected to a display unit such as a monitor MT. Via said back end graphical user interface (UI) generator GG is capable of producing a video signal which when displayed on the screen shows a graphical user interface GUI that supports an intervention by quickly allowing the interventionalist to navigate to a desired target site within the object OB.

The graphical user interface GUI so produced includes as basic widget components two windows or panes, one being a navigational window NC for the current position of the tool IT within the object OB, the other being an explorative window PC in which the information gathered by this spectral analyzer is shown in a suggestive and condensed manner so as to allow physicians finding their way quickly around.

Figure 2:
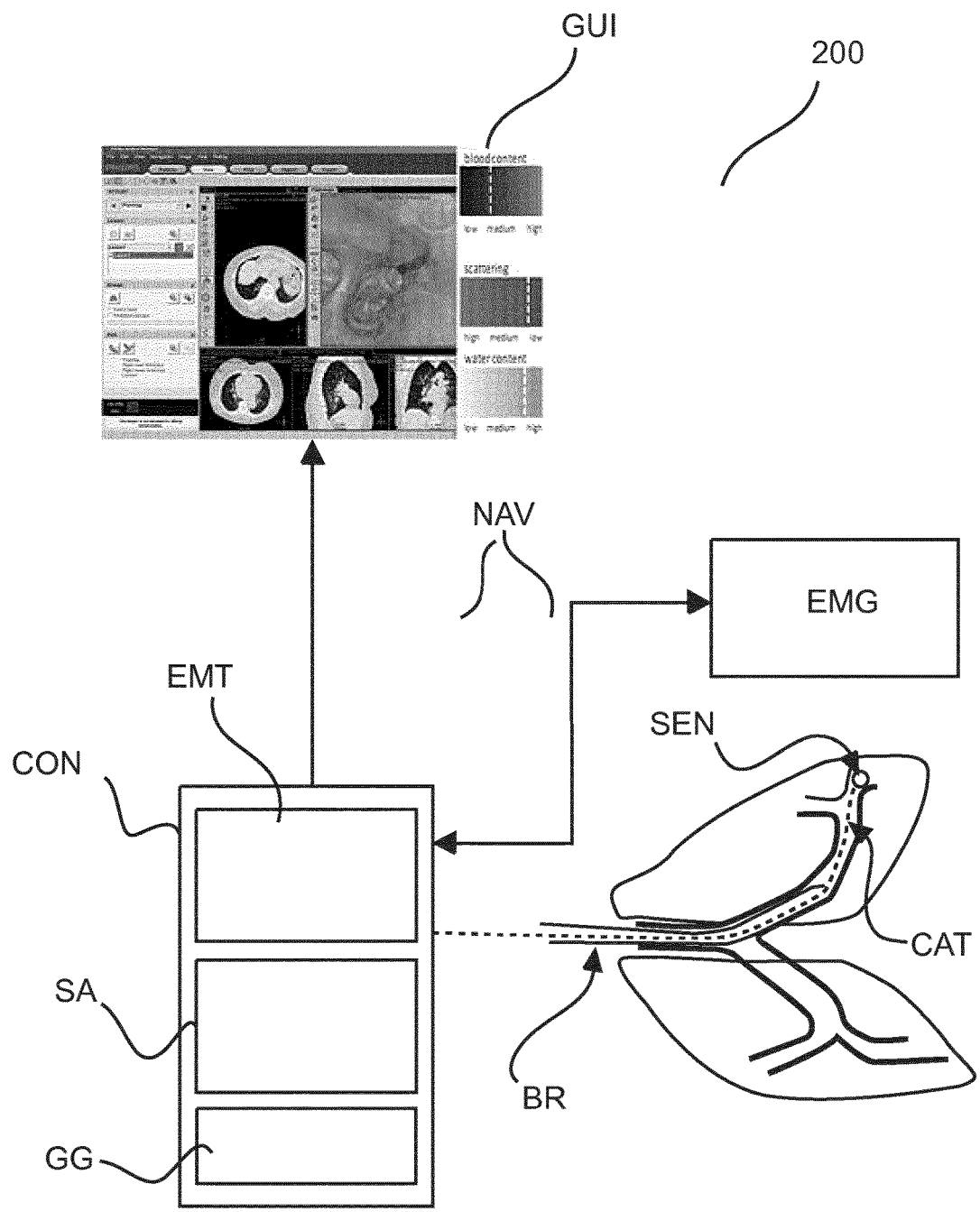
FIG. 2 shows an embodiment of the system in FIG. 1.

With reference to FIG. 2 there is shown an embodiment of FIG. 1 in the context of a bronchoscopy intervention.

As can be seen, in one embodiment the spectral analyzer SA and the navigation component NAV are integrated in a common housing, namely a console CON, which may be portable (but not necessarily so) and may include its own display unit MT although more traditional desktop type embodiments are also envisaged where the components are coupled via a computer system (such as a workstation of the relevant imaging modality) to a monitor MT of said computer system.

A bronchoscopy is carried out on the lung shown diagrammatically on the lower right side of FIG. 2. The bronchoscope BR is essentially a flexible tube ("working channel") that can be introduced into the bronchi of the patient however only up to a certain point due to space restrictions.

A flexible, steerable catheter CAT can then be guided or "snaked" through the bronchoscope's working channel towards a site within the lung from which a biopsy is to be taken. As the bronchoscope cannot assess the finer bronchi of the patient the steerable catheter point is to leave the bronchoscope that it extends beyond the terminal portion of the bronchoscope into the bronchi of the patient.

The tip portion of the catheter includes an EM optical sensor SEN (essentially a coil) that is coupled wirelessly to an EM tracking device.

FIG. 2 shows one embodiment of the EM tracked navigation bronchoscopy set up. It consists of a field generator EMT that creates a spatially varying electromagnetic field. The generator is coupled to integrated in console CON. When the catheter CAT (and with it the sensor SEN) is placed inside the object OB (in this case, is inserted into the patients lung), controlled, varying magnetic fields, and voltages are induced in the sensor coils. These induced voltages are used by a signal processing component of the EM Navigation component NAV to calculate the position and orientation of the senor and hence the tool tip. Location measurement of the tool within the surrounding object OB is possible without the line-of-sight constraints.

The UI generator GG is configured to receive the processed signal for the EM tracking sensor SEN mounted at the proximal tip of biopsy device. In one embodiment, the biopsy device IT can be a steerable catheter CAT that can be inserted through the working channel of the flexible bronchoscope BR.

First, the a pre-operative CT or other image such a planar X-ray image is spatially registered onto the EM tracking space, which is the live tracking space, defined by the varying EM field. This initial registration is used to display the current position of the tracked catheter overlaid at the correct position in the pre-operative imagery (that is, not a live image). The information from the EM tracking component and the exploratory information from the spectral analyzer SA optical sensor is synchronized and then sent over to the UI generator to produce the GUI for live display on monitor MT.

Figure 13:
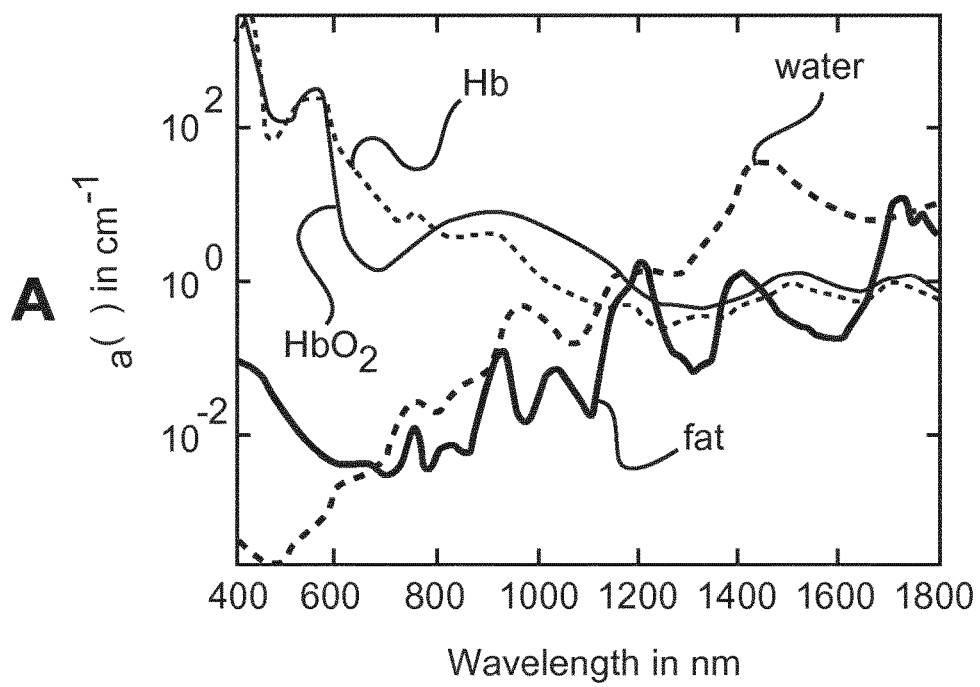
FIG. 13 shows spectra of different tissue types.
Figure 13:
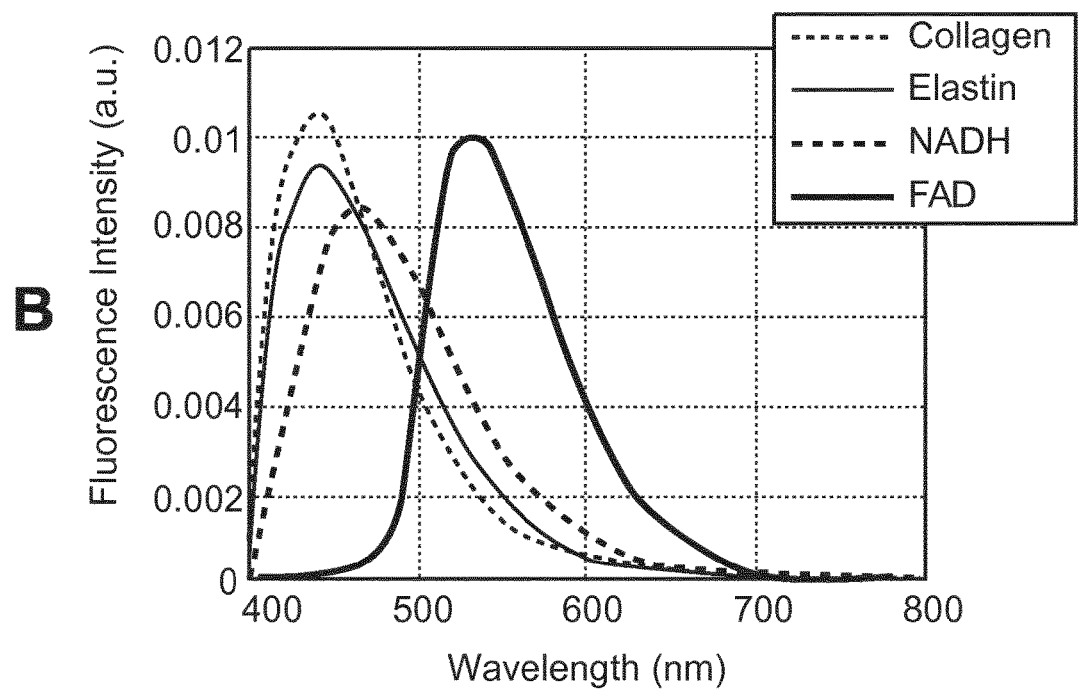

Before explaining operation of UI generator GG in more detail, operation of the spectral analyzer SA is explained in more detail with reference to FIGS. 3 and 13.

Broadly, the spectral analyzer is capable of sending and receiving light through the probe integrated in the interventional tool. The light is received after having interacted with the tissue near the interventional device. The probe PR in the interventional too contains one or more waveguides, with a proximal and a distal end. The distal end is capable of sending the light from the analyzer SA into the tissue. The distal end is furthermore capable of capturing the reflected light (after interaction with the tissue) and of sending the reflected light back to the analyzer SA. The spectral analyzer SA includes a signal processing backend capable of spectrally analyzing the received light which allows determining in one embodiment the scattering coefficient, and physiological parameters or interest such as the hemoglobin concentration and water concentration of the tissue, as well as any other optical absorber or interest.

Figure 3:
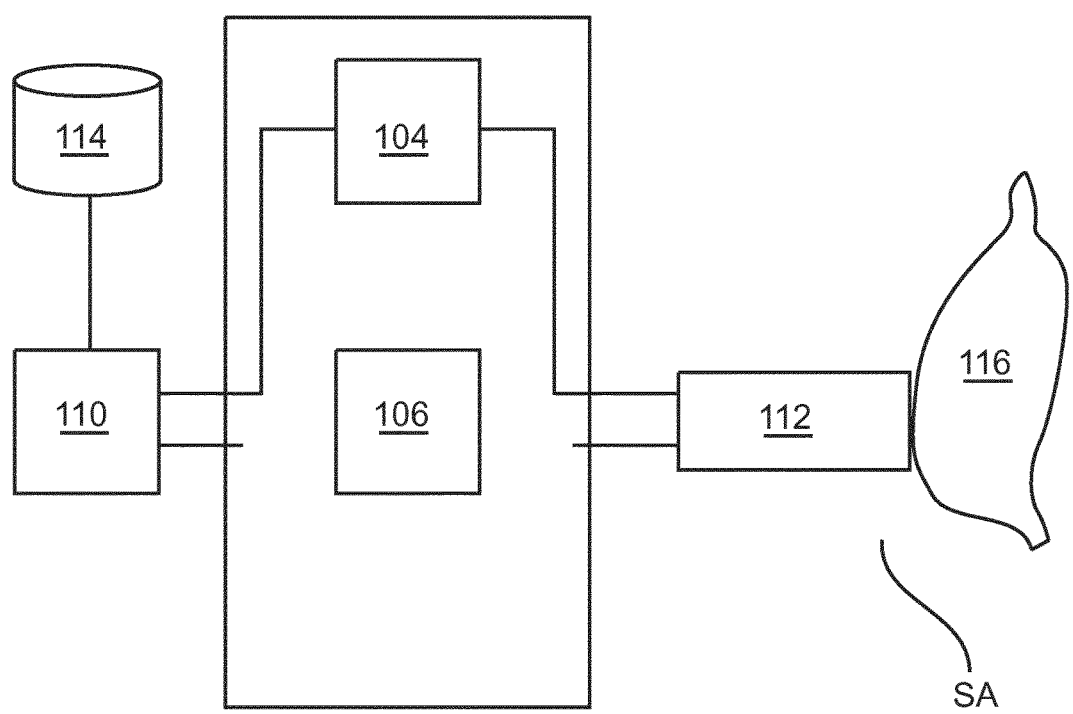
FIG. 3 shows a block diagram of a spectral analyzer used in the system of FIG. 2.

Explaining now operation of SA analyzer in more detail with reference to FIG. 3, the probe PR contains two light guides terminating in light entrance ports at the distal end. These light guides of the probe are connected to the spectral analyzer SA. These light guides are understood to be for instance optical fibers or optical waveguides. In a specific embodiment and as shown in FIG. 3, spectral analyzer comprises a light source 104 in the form of a halogen broadband light source with an embedded shutter and the probe PR, 112, possibly integrated or inserted into the interventional device IT. An optical detector 106 is configured to resolve light with a wavelength substantially in the visible and infrared regions of the wavelength spectrum, such as from 400 nm to 1700 nm. The combination of 104 and 106 allows for diffuse reflectance (DRS) and fluorescence measurements on tissue 116. For a detailed discussion on DRS measurements see R. Nachabé et al in "Estimation of biological chromophores using diffuse optical spectroscopy: benefit of extending the UV-VIS wavelength range to include 1000 to 1600 nm," Optics Express, vol. 18, 2010, pp. 879-888 or R. Nachabe, et al in "Estimation of lipid and water concentrations in scattering media with diffuse optical spectroscopy from 900 to 1600 nm," Journal of Biomedical Optics, vol. 15, May. 2010, pp. 037015-10. From these DRS measurements, tissue transitions (i.e. benign to malignant) can be deduced.

Although diffuse reflectance spectroscopy is described above to extract tissue properties, other optical methods can also be envisioned like diffuse optical tomography by employing a plurality of optical fibers, differential path length spectroscopy, fluorescence and Raman spectroscopy. Additionally, acquisition of optical data could be done via a probe that is contact with the tissue or via a non-contact probe.

A processor 110 transforms the measured spectra as detected by sensor 106 into physiological parameters that are indicative of the tissue state for the source-detector fiber combination. The information is then used to visualize the transitions according to the invention. To determine whether a certain tissue is in front of the needle, the signal for each source-detector pair can be compared with a look-up-table held in a database 114. Another way is to translate the measured parameters into physiological parameters and define ranges for these parameters for each tissue type. See for instance R. Nachabé, et al in "Diagnosis of breast cancer using optical spectroscopy from 500 to 1600 nm: a comparison of classification methods", J. Biomed. Opt. 16 (2011) 087010, where methods based on classification and regression tree (CART) analyses are described for classifying tissue based on these physiological parameters. In sum, the exploratory information as supplied by spectral analyzer SA identifies the tissue type (more particularly the material/chromophore type) currently present around the probes PR tip and computes the amount thereof suitably expressed as a density, concentration etc. Furthermore, the spectral analyzer determines the scattering properties of the tissue. Because the probe PR is so arranged that its light entrance ports come to lie at the tip or working part of the interventional tool (e.g., biopsy needle or injection needle) the tissue type and amount registered can be taken to be that in front of the working part of the tool IT.

According to one embodiment, spectral analyzer SA includes an extractor module configured to extract the physiological parameters (such as blood water) and/or scattering by fitting the acquired spectra to a model. In one embodiment the algorithm for the extractor module is programmed using the Matlab® suite by Mathworks, Natick, Mass., USA. In this algorithm, a widely accepted analytical model was implemented, namely the model of T. J. Farrel, M. S. Patterson and B. C. Wilson, in "A diffusion theory model of spatially resolved, steady-state diffuse reflectance for the non-invasive determination of tissue optical properties," Med. Phys. 19 (1992) p. 879-888, which is hereby incorporated by reference in its entirety.

The input arguments for the model of Farrel et al are the absorption coefficient $\mu_\alpha(\lambda)$, the reduced scattering coefficient $\mu_s'(\lambda)$ and the center-to-center distance between the emitting and collecting fibers at the tip of the probe. For a complete description of the diffusion theory model, we refer again to R. Nachabé et al in "Estimation of biological chromophores using diffuse optical spectroscopy: benefit of extending the UV-VIS wavelength range to include 1000 to 1600 nm," Optics Express, vol. 18, 2010, pp. 879-888 or R. Nachabe, et al in "Estimation of lipid and water concentrations in scattering media with diffuse optical spectroscopy from 900 to 1600 nm," Journal of Biomedical Optics, vol. 15, May. 2010, pp. 037015-10.

In the following, the model will be explained briefly. The following equations (1)-(6) are mainly based on the two previously cited references of Nachabé et al., which are hereby both incorporated by reference in their entirety.

It has been found that a double power law function can be used to describe the wavelength dependence of the reduced scattering coefficient, where the wavelength $\lambda$ is expressed in nm and is normalized to a wavelength value of $\lambda_0=800$ nm. The parameter $\alpha$ corresponds to the reduced scattering amplitude at this specific wavelength.

$$\mu_s'(\lambda) = a\left(\rho_{MR}\left(\frac{\lambda}{\lambda_0}\right)^{-b} + (1-\rho_{MR})\left(\frac{\lambda}{\lambda_0}\right)^{-4}\right) [\text{cm}^{-1}] \quad \text{Eq (1)}$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted as b and is related to the particle size.

For a homogeneous distribution of absorbers, the total light absorption coefficient $\mu_\alpha(\lambda)$ can be computed as products of the extinction coefficients and volume fraction of the absorbers (see FIG. 13A):

$$\mu_\alpha^{Total} = f_1\mu_\alpha^1 + f_2\mu_\alpha^2 + f_3\mu_\alpha^3 + \ldots \quad \text{Eq(2)}$$

Instead of modeling the absorption coefficient $\mu_\alpha(\lambda)$ as the sum of absorption coefficients weighted by the respective concentrations of the four chromophores of interest, it was decided to express the tissue absorption coefficient as $$\mu_\alpha^{Tissue}(\lambda) = C(\lambda)v_{Blood}\mu_\alpha^{Blood}(\lambda) + v_{WL}\mu_\alpha^{WL}(\lambda)[\text{cm}^{-1}] \quad \text{Eq(3)}$$

, where $\mu_\alpha^{Blood}(\lambda)$ corresponds to the absorption by blood and $\mu_\alpha^{WL}(\lambda)$ corresponds to absorption by water and lipid together in the probed volume. The volume fraction of water and lipid is $v_{WL}=[\text{Lipid}]+[\text{H}_2\text{O}]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1-\exp(-2R\,\mu_a^{Blood}(\lambda))}{2R\,\mu_a^{Blood}(\lambda)}, \quad \text{Eq (4)}$$

where R denotes the average vessel radius expressed in cm. The absorption coefficient related to blood is given by $$\mu_\alpha^{Blood}(\lambda) = \alpha_{BL}\mu_\alpha^{HbO_2}(\lambda) + (1-\alpha_{BL})\mu_\alpha^{Hb}(\lambda)[\text{cm}^{-1}] \quad \text{Eq(5)}$$

, where $\mu_\alpha^{HbO_2}(\lambda)$ and $\mu_\alpha^{Hb}(\lambda)$ represent the basic extinction coefficient spectra of oxygenated hemoglobin $HbO_2$ and deoxygenated hemoglobin Hb, respectively. The oxygenated hemoglobin fraction in the total amount of hemoglobin is noted as $\alpha_{BL}=[HbO_2]/([HbO_2]+[Hb])$ and is commonly known as the blood oxygen saturation. The absorption due to the presence of water and lipid in the measured tissue is defined as)

$$\mu_\alpha^{WL}(\lambda) = \alpha_{WL}\mu_\alpha^{Lipid}(\lambda) + (1-\alpha_{WL})\mu_\alpha^{H_2O}(\lambda)[\text{cm}^{-1}] \quad \text{Eq(6)}$$

In this case the concentration of lipid related to the total concentration of lipid and water together can be written as $\alpha_{WF}=[\text{Lipid}]/([\text{Lipid}]+[\text{H}_2\text{O}])$, where [Lipid] and [$\text{H}_2\text{O}$], correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit. The output of the fitting operation is then in inter alia the sought after water data $\mu^{H_2O}$ and/or lipid data.

See the Nachabe et at published in Optics Express referenced above. For further explanation and validation of this theorem cf Nachabe et al. published in "Journal of Biomedical Optics" referenced above.

Another way to discriminate differences in spectra is by making use of a principal components analysis. This method allows classification of differences in spectra and thus allows discrimination between tissues.

Other optical absorbers could also be incorporated into this algorithm, such as: lycopene, vitamin A, β-carotene, bile, or black tar (or any absorbing substance related to smoking).

Apart from diffuse reflectance we could also measure fluorescence. Then for instance parameters like collagen, elastin, NADH and FAD could be measured too (see 13B). The ratio NADH/FAD, which is called the optical redox parameter, is of interest because it is an indicator for the metabolic state of the tissue. See also the approach in M. Müller and B. H. W. Hendriks, "Recovering intrinsic fluorescence by Monte Carlo modeling", J. Biomed. Optics vol. 18 (2013) p. 027009-1 to 027009-13, which can also be used to discriminate tissues.

Operation of the graphical user interface generator GG will now be explained in more detail with reference to the following FIGS. 4-8 showing various graphical user interfaces produced by the graphical user interface generator GG.

Figure 4:
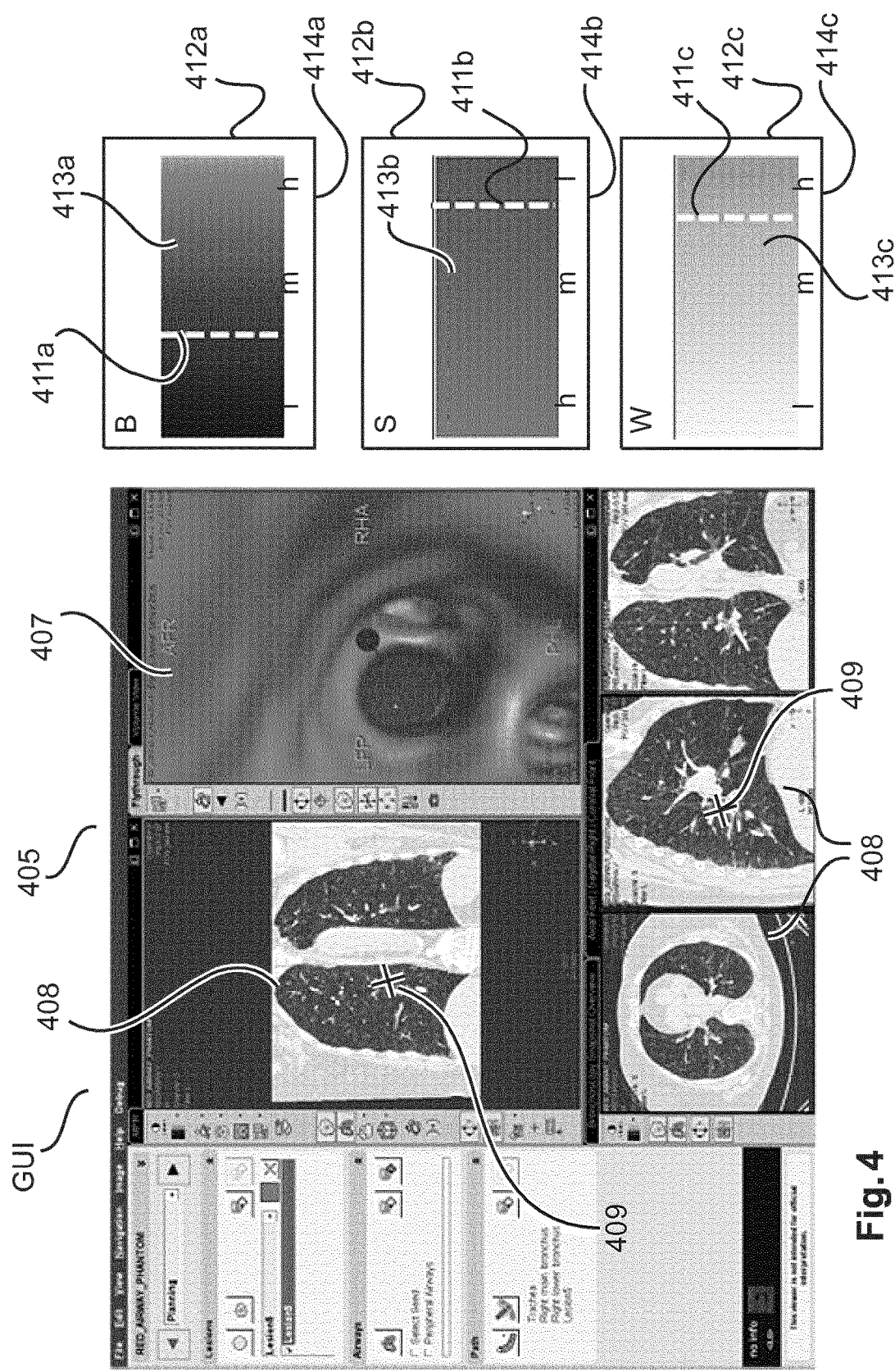
FIG. 4 shows a graphical user interface according to a first embodiment produced by the system of FIG. 2.

A view of user interface GUI according to a first embodiment as produced by the UI generator GG of FIG. 2 is shown in FIG. 4. In the first embodiment we make use of a user interface that consists of several windows (see FIG. 1 and FIG. 2).

In the navigation window NC there is displayed the electromagnetic tracking information produced by the EM device overlaid on various pre-interventional imagery 407, 408 of the ROI, with position indicator 409 indicating the current position of the interventional tool's IT tip TP. In FIG.

5, the navigation window NC is multi-pane, with one or more panes 408 showing planar projection images acquired along different projection directions. Pane 407 furnishes a 3D volumetric reconstruction from pre-interventional CT projection images adding a "virtual" look-and-feel to the GUI.

The exploratory window PC is made up of several widgets 412a-c, in which there is shown a graphical rendering of the optical information gathered by the spectral analyzer SA in form of current hemoglobin concentration B, water concentration W, and scattering S amount, each as per the current position of the PR. Both, the position indicator and the optical information (that is, the exploratory information) are real-time updated as the tool IT or the PR is made to change position.

Each of these optical parameters B, W, and S is displayed as a respective, color-coded bar element 413a-c the bar element forms a rectangular dial that indicates the ranges in color- or grey value coded manner across the bar element. There is also a basic graduation 414a-c to indicate magnitude other than by color. For instance, the values can range from low "l" through medium "m" to high "h". A pointer line (shown in FIG. 1 and FIG. 2 as a dashed line) marks the current value for each of the optical parameters. This pointer line 411a-c "shifts" as the interventional tool is moved to different tissue sites not unlike a needle in a gauge indicator for pressure or speed measurements. The physician can then make a decision of whether to biopsy the current site based on his/her assessment of these optical parameters.

In the current situation as shown in FIG. 4 (which represents a snapshot at a certain instance during the intervention), there is relatively low blood content which indicates there is no bleeding present at the tip of the probe PR. The rather high scattering and medium water content show that the probe still resides in non-malignant lung parenchyma.

Figure 5:
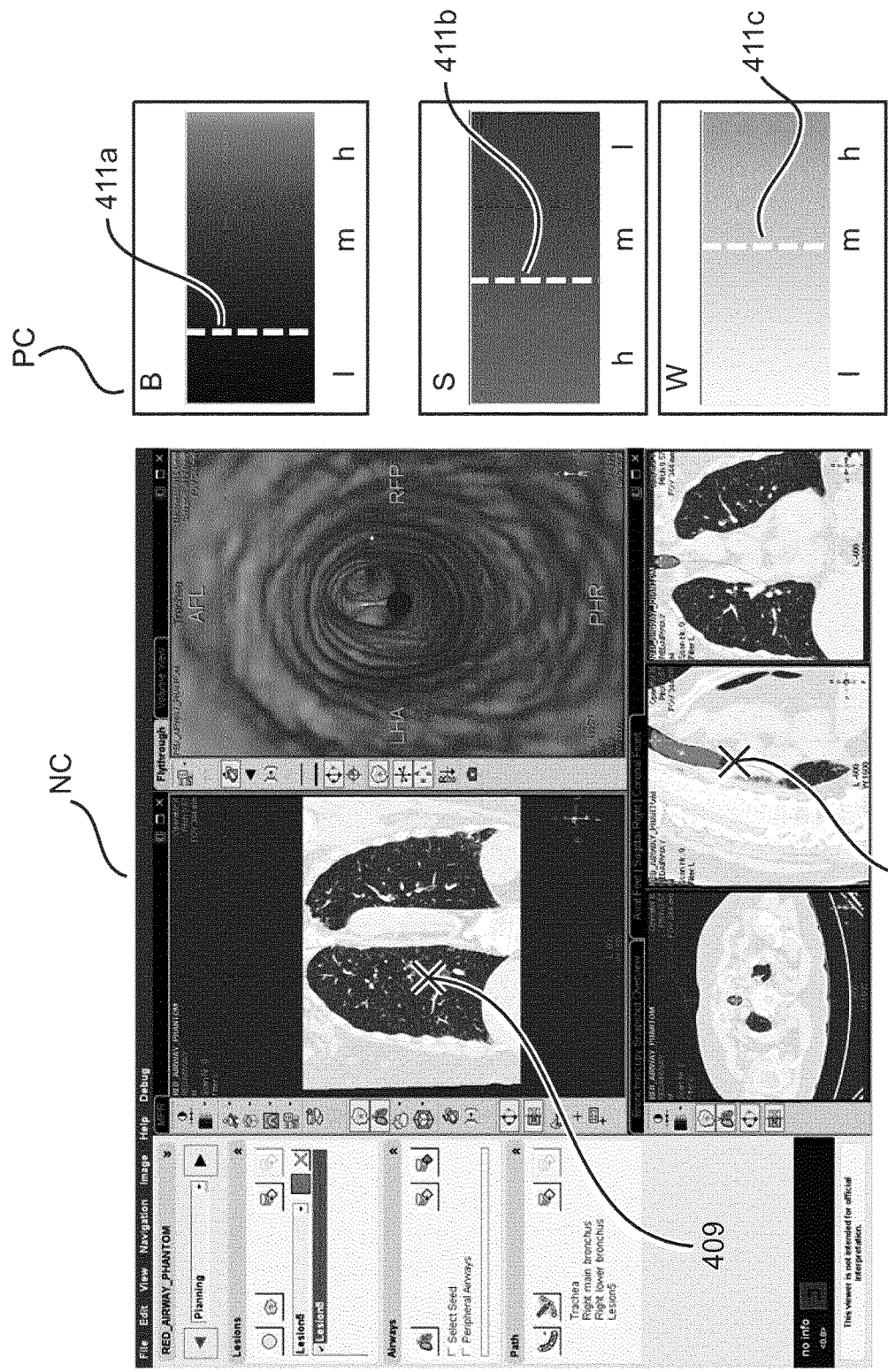
FIG. 5 shows a graphical user interface of FIG. 4 in a different state and/or at a different time instance.

FIG. 5 illustrates GUI of FIG. 4 at a later time instance when the tool IT/probe PR has been moved to a different position in the lung. There is still low blood content (so still no bleeding present), but now the low scattering and high water content show that the probe is no longer in normal lung parenchyma, i.e. target (malignant tissue) has been reached. The catheter can now be actuated to biopsy the tissue at the current tool IT position.

Figure 6:
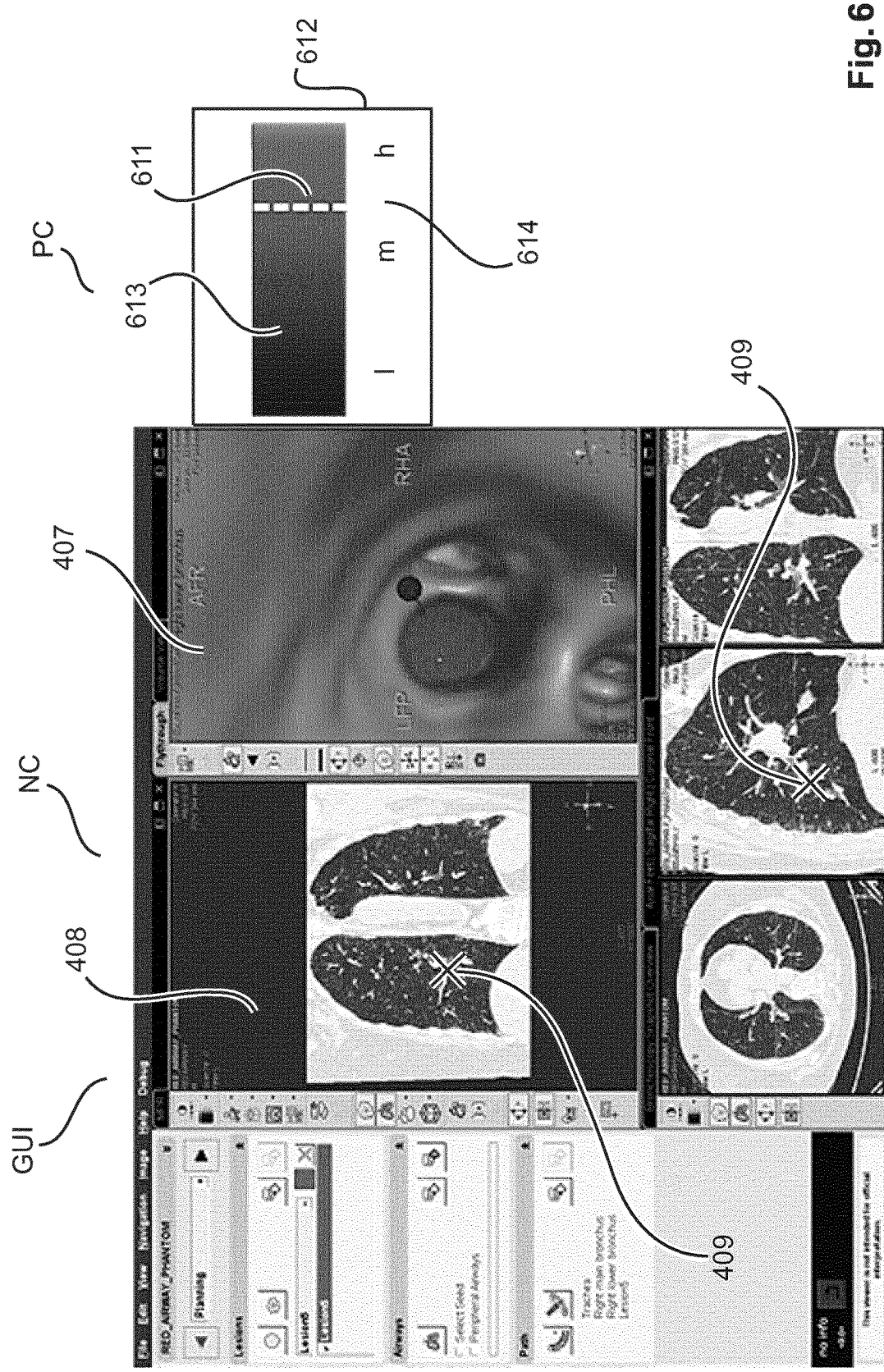
FIG. 6 shows a graphical user interface according to a second embodiment as produced by the system in FIG. 2.

FIG. 6 shows a view of a GUI according to a second embodiment. The embodiment is in general similar to the one shown in FIGS. 4,5, but now the exploratory information on the three optical measurements B, W and S is consolidated into a single bar element 613 in a single indicator widget 612.

More particularly, color-coded dial bar 613 function as a dial and represents a super-parameter which is constructed from a suitable arithmetic combination of the optical absorbers (e.g. hemoglobin B, water W, scattering S, or others). According to one embodiment, to computation of the super-parameter is achieved as:

$$\text{super-parameter} = (\text{hemoglobin saturation}) \times \frac{\text{water (concentration)}}{\text{(amount of) scattering}} \quad \text{Eq (7)}$$

The three optical parameter B, W and S and in particular their combination as per (7) has been found to allow excellent discrimination of malignant from non-malignant tissue in particular (but not only) for lung tissue. In equation (7), "hemoglobin saturation" measures the amount of blood that is bound to oxygen (then forming $HbO_2$). In a deoxygenated state no or only a small amount of blood is so bound.

As in FIGS. 4,5, navigation window NC displays the EM-tracking information while in the exploratory window widget 612, the single bar element 613 is displayed where the values can range from low "l" through medium "m" to high "h" as indicated by graduation 614. The super-parameter is so scaled and mapped, that a high value (right hand side of bar or dial 613) for the super-parameter is indicative of malignant tissue.

In one embodiment, the color-coding of bar 613 and the ranges as per graduation 614 are scaled to represent the probability that the tissue is malignant. The probability would be formed from an a priori classification database. Again, a vertical line pointer marks the current value for the super-parameter/probability. This line is recomputed by UI generator GG to effect a "shift" as the interventional tool is moved to different tissue sites. The physician can then make a decision of whether to biopsy the site based on his/her assessment. The single widget 612 with the super parameter may be displayed instead of the dedicated widgets 412a-c of FIG. 4 or in addition thereto.

Figures 7, 7A:
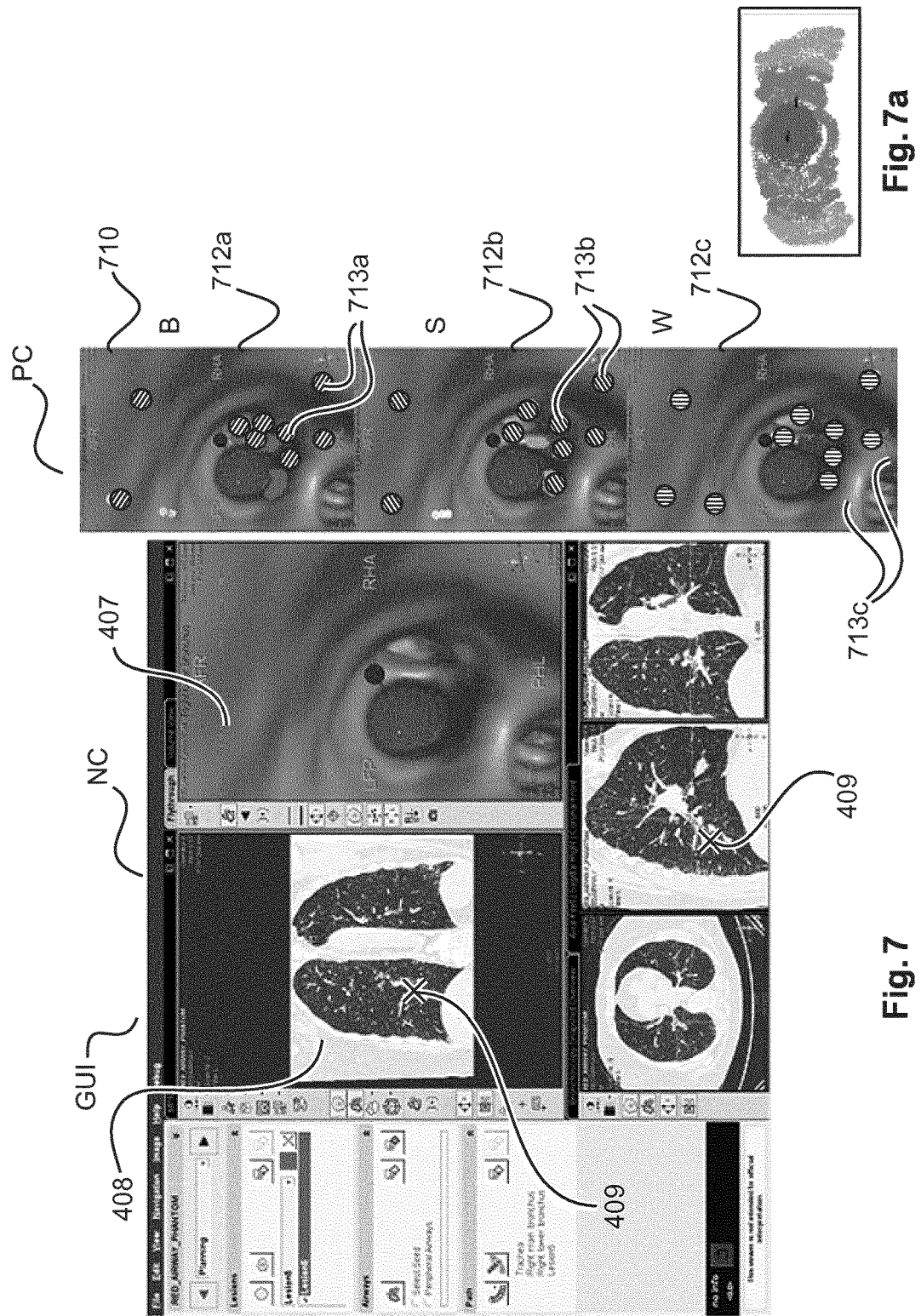
FIG. 7 shows a graphical user interface according to a third embodiment produced by the system of FIG. 2.

FIG. 7 shows a view of a GUI according to a third embodiment.

As in the previous embodiments, in the spatial navigation window NC the EM-tracking information is displayed overlaid on previously recorded imagery 408 an/or reconstruction imagery 407.

The exploratory window PC now comprises one or more (for instance three) additional windows or panes 712a-c each including a copy of a "virtual" image as per 407 (created from the EM-tracking data and the pre-interventional reconstructions) or any other imagery of the object's interior that corresponds to the current position of the tool IT and probe PR. Each copy is overlaid, possibly multiple times, with respective 713a-c markers that represent (by color- or shape coding) the optical parameters such as blood or water content or scattering. More specifically, a respective marker dot or blob 713a-c will appear overlaid on the virtual image at a spatially correct location that corresponds to the site where the respective optical measurement was taken. The optical information in form of respective measurement values are accumulated as the measurements progresses whilst the tool IT/probe PR changes position. The measurement values W, B, S can be stored to essentially create a 3D optical image of the morphology in terms of tissue type or material composition. The more sites are measured, the more markers 713a-c will accumulate and the more "colorful" the overlaid images 713a-c will become. A suitably suggestive color palette for the encoding may be chosen such as red for blood B, blue for water W and green or otherwise for scattering S. The color or grey-values are presented in "gradient form", that is a brighter hue of the respective color for W, B and S will indicate a respectively higher value of the optical parameter and thus a higher concentration or density or other prevalence or magnitude. Other than by color or by color only, the values may also be encoded by markers 713a-c of different shapes with magnitude being encoded by variation of size of the respective shape.

Making multiple optical measurements with the spectral analyzer SA will result in the building up of a 3D map of tissue types/scattering prevalence which the physician can then use to determine where to biopsy the tissue and/or where to leave a bio-marker behind for future treatments.

A biopsy and marker placement could be done at the center of the suspicious lesion as defined by the marker blobs 713a-c. Also at the boundary of the lesion may be discernible from patterns formed by the overlaid maker blobs 713a-c as depicted in inset FIG. 7A.

As a variant to the FIG. 7 embodiment, and similar to what has been explained above in relation to the GUI in FIG. 6, instead of dedicated makers for the optical parameters, the single, super-parameter or a probability value may be encoded instead by the marker blob. In this case there will be a single widget with the virtual image overlaid with the maker blob encoding magnitude of the super-parameter by size/shape/color/grey value as recorded at the respective site. Also, instead of the super parameter, the probability value may be encoded to so build up a 3D probability map.

Figure 8:
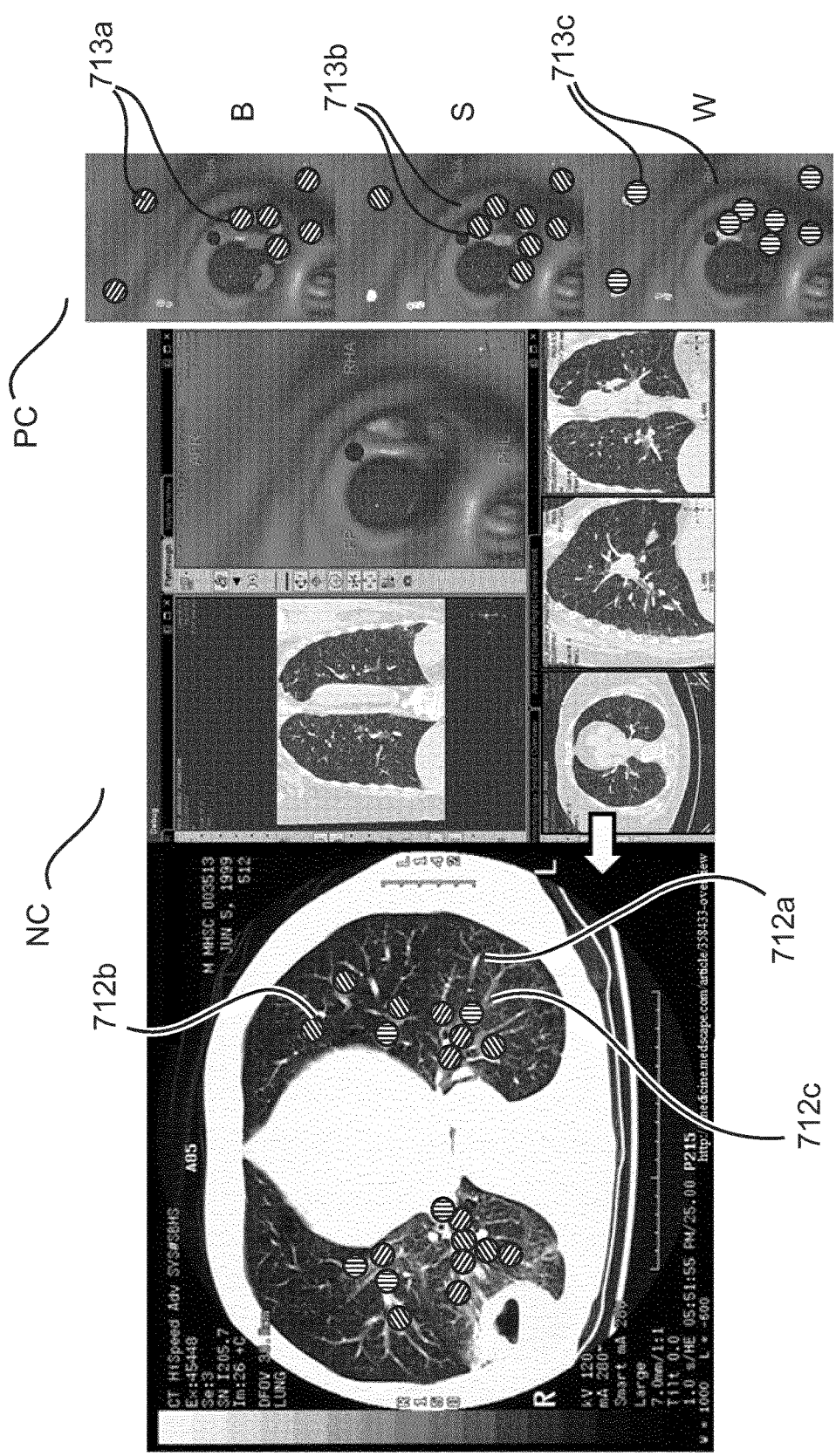
FIG. 8 shows a graphical user interface according to a fourth embodiment produced by the system of FIG. 2.

FIG. 8 shows a view of a GUI according to a fourth embodiment similar to the FIG. 7 embodiment. In this embodiment, the optical parameters or the super parameters are displayed in the navigation window NC overlaid on the navigation imagery such as the X-ray projection images in addition to the EM-tracked images. The visualization of the optical parameters against the imagery (such the x-ray image) provides a global perspective of distribution of these parameters (and hence of the distribution of blood content, scattering and water content) in the lung. The marker blobs 712a-c may also be overlaid at corresponding positions across on different cross sections of the X-ray images to obtain a 3-dimensional view. This embodiment may be used with benefit in treatment planning As mentioned, the measurement markers 713a-c for visual recordal of the respective measurements at the various positions are shown in addition to the pointer-versus-dial bar elements widgets 412a-c or 612 of the FIG. 4 or 6 embodiments, respectively. For ease of representation however, said bar elements are not shown in FIGS. 7, 8. For instance, the row of bar elements of FIG. 4 or the super-parameter window of FIG. 6 may be displayed alongside the row of panes 712a-c of FIG. 7 each including the respective copies of the CT imagery with the overlaid markers 713a-c. The FIG. 8 embodiment, may be combined with either or the FIG. 4 or 6 embodiment, where the markers 712a-b are shown overlaid in imagery of the navigation window NC.

Figure 9:
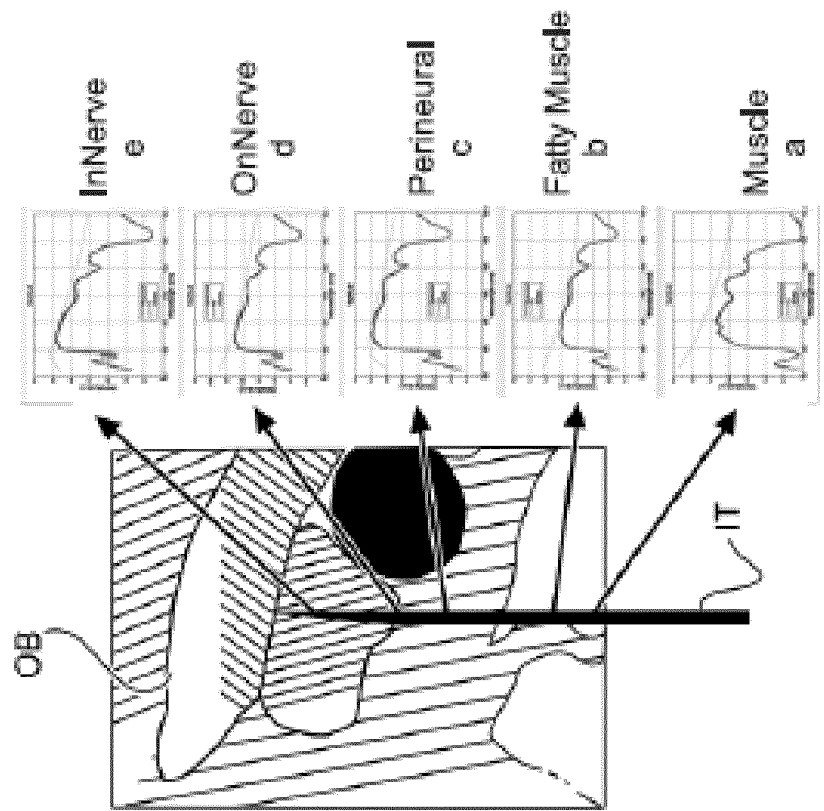
FIG. 9 shows a biopsy needle in its passage through a stratified environment.
Figure 9:
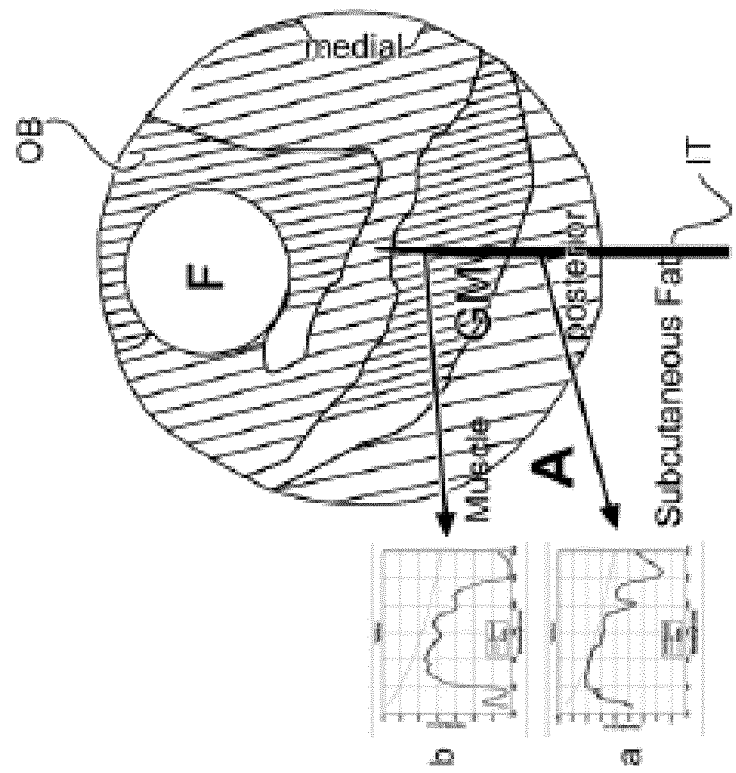

With reference to FIG. 9 there is shown a different context in which the proposed system of FIG. 1 can be put to good use. The figure shows the interventional tool as a biopsy needle that includes a spectral analyzer facility in particular an optical guide wire built into the tip of the needle which runs along and inside the needle out to the spectral analyzer. The figure schematically shows the needle in its passage through stratified structure, for instance skin-fat-muscle transitions. The characteristic spectra of the tissue type encountered at the tip in its passage through the various strata are shown as spectral curves a-b of the left hand side and a-e on the right hand side.

Figure 10:
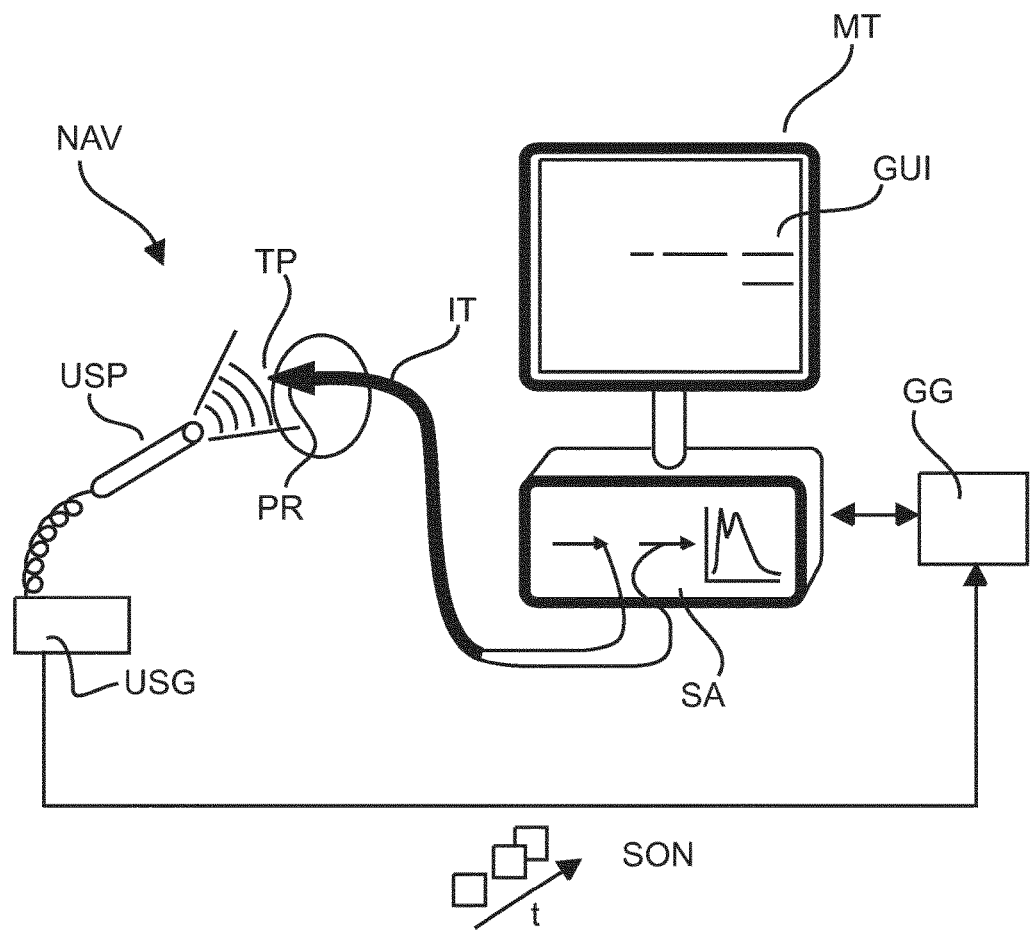
FIG. 10 shows a system of FIG. 1 according to a second embodiment.

With reference to FIG. 10 there is shown the system of FIG. 1 according to a second embodiment. In particular the system in FIG. 10 is for supporting the regional administration of an anesthetic.

The navigation component NAV in this embodiment is ultrasound imaging equipment USD that includes an ultrasound probe USP that is position able in any desired position or orientation relative to patient PAT. The probe USP is configured to transmit ultrasound pulsed waves which are bouncing off structures in the patient's anatomy. The probe is further configured to register the bounced off waves as incoming echo sound waves and a processor in the equipment calculates the travel time of said incoming echo waves to form a series of sonograms SON for sequential time instants t. The sonograms SON when rendered into "live" imagery for display on monitor MT show the tip TP thereby affording to the physician a "coarse" orientation means. A finer graduation of navigation is then afforded by the spectra analyzer as previously described with reference to the embodiments as per FIG. 2.

In an alternative embodiment (not shown), the navigation component NAV is a fluoroscopy imaging device, for instance an interventional a C-arm imager FIM, a common piece of equipment in nowadays' cath labs. Very briefly, an x-ray source and a detector mounted in opposed relationship on a rotatable "C" or "U"-shaped arm slide able held in a cradle. The C-arm, and with it the x-ray source and the detector, can be rotated around the patient and/or the site or region of interest. The fluoroscopy system outputs a series of live images (fluorograms) that show the radiation opaque needle tip TP in a projection image thereby affording the physician a similarly "coarse" orientation means as the ultrasound equipment USG. Other modalities such as CT or MRI etc. are also envisaged.

Figure 11:
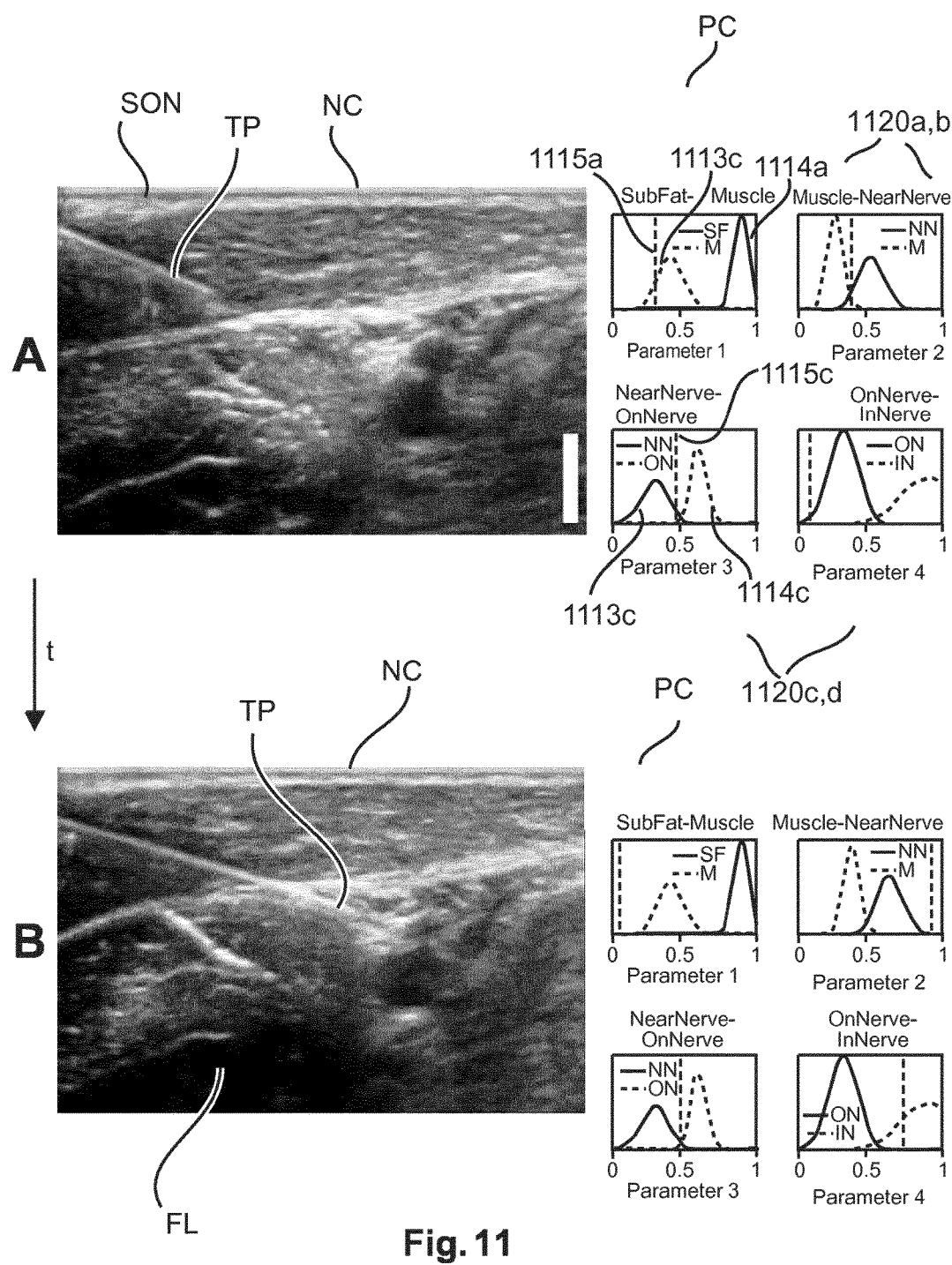
FIG. 11 shows two views at different instances in time of a graphical user interface according to a first embodiment produced by the system of FIG. 10.

A view of user interface GUI according to a further embodiment as produced by the UI generator GG in the system of FIG. 10 is shown in FIG. 11. The GUIs are explained with reference to the ultrasound example but this is merely one embodiment and not limiting. The GUIs proposed in the following are particularly useful when exploring stratified object parts across a plurality of its strata.

Broadly, in this embodiment, in the navigation window NC there is shown preferably live imagery SON acquired by the ultrasound device. Along with the navigation window NC, the exploratory window PC now includes one or more sub-windows or panes 1120a-c, each dedicated and linked to a different tissue transition.

These tissue transitions will be described by a relevant optical parameter P1-4 which is related to a physiological or scattering parameter or some combination thereof as described above in FIG. 3 and in the bronchoscopy embodiments in FIGS. 2, 4-8.

For instance, the parameter P1 will be displayed as a probability distribution or density function (PDF) for tissue of a first type #1 and tissue of a second type #2 in the transition: Hence two PDF curves 1113a,1114a will be shown in each respective window (for instance 1120a) where the graduation along x-axis is the value of the parameter and the y-axis is the probability or density concentration, that is, the likelihood. Similar for the other transition panes 1120b-d. The PDF will be determined from a predefined database holding historical spectral measurement classified as per tissue types.

Apart from these two predefined distributions, a vertical pointer line 1115 is displayed that corresponds to the current value of the optical parameter P1 that is being measured by the probe PR. From the first window NC affords a "coarse" orientation, as the physician can determine anatomically which transition is likely to occur. From the corresponding additional windows 1120a-d in pane PC, more detailed, "finer" information regarding the transition can be determined. Both information streams allow the physician to assess the likelihood of the needle position IT with respect to the tissue transition. The optical parameter P1 used for the above tissue transitions, may include any one of or a combination of any of the following: amount of blood, blood oxygenation (that is, saturation), water content/amount, scattering, lipid content.

In the embodiment of FIG. 11, a Gaussian shaped distribution or density plot as a function of one relevant parameter (x-axis in appropriately scaled graduation) is shown although other distribution densities are also envisaged herein. The height of the Gaussian (along y-axis) corresponds to the likelihood for the parameter to correspond to that tissue type. The center of the Gaussian distribution is related to the value which is on average typical for the tissue type. The width of the Gaussian distribution is related to the spread this parameter has for this tissue. In this way, each tissue type has a Gaussian distribution for each parameter. In a window there are then two different Gaussian distributions linked to the two different tissue types in a transition. The GUI furnishes the following information: Comparing each of the panes 1120a-d dedicated to a specific tissue transition, the Gaussian density is identified by visual inspection that is closest to the respective pointer line 1115a,c (designated in the figure exemplary for pane 1120a,c, respectively). The tissue associated with said Gaussian is then an indication for the current tissue at the needle tip TP at the current position of the biopsy device IT. Association between the probability densities is either by color-coding (which is maintained consistently for each tissue throughout the different transition panes 1120a-d) or line types (dashed, dotted etc.) as indicated in the figure. In the present medical context and as explained in FIG. 9, there are 5 strata (sub-fat, muscle, near nerve, on nerve and in nerve) which results in 4 distinguishable transitions (not counting respective opposite transitions), hence 4 panes 1120a-d are shown in FIG. 11. FIG. 11 A shows an instance where a transition from muscle tissue to near nerve is likely whereas FIG. 11 B shows a view at an instance where the needle IT likely resides in a region that corresponds to a transition from on nerve to in nerve is likely. The number and nature of transition and tissue types are purely for illustrative purposes and are in no way limiting.

Figure 12:
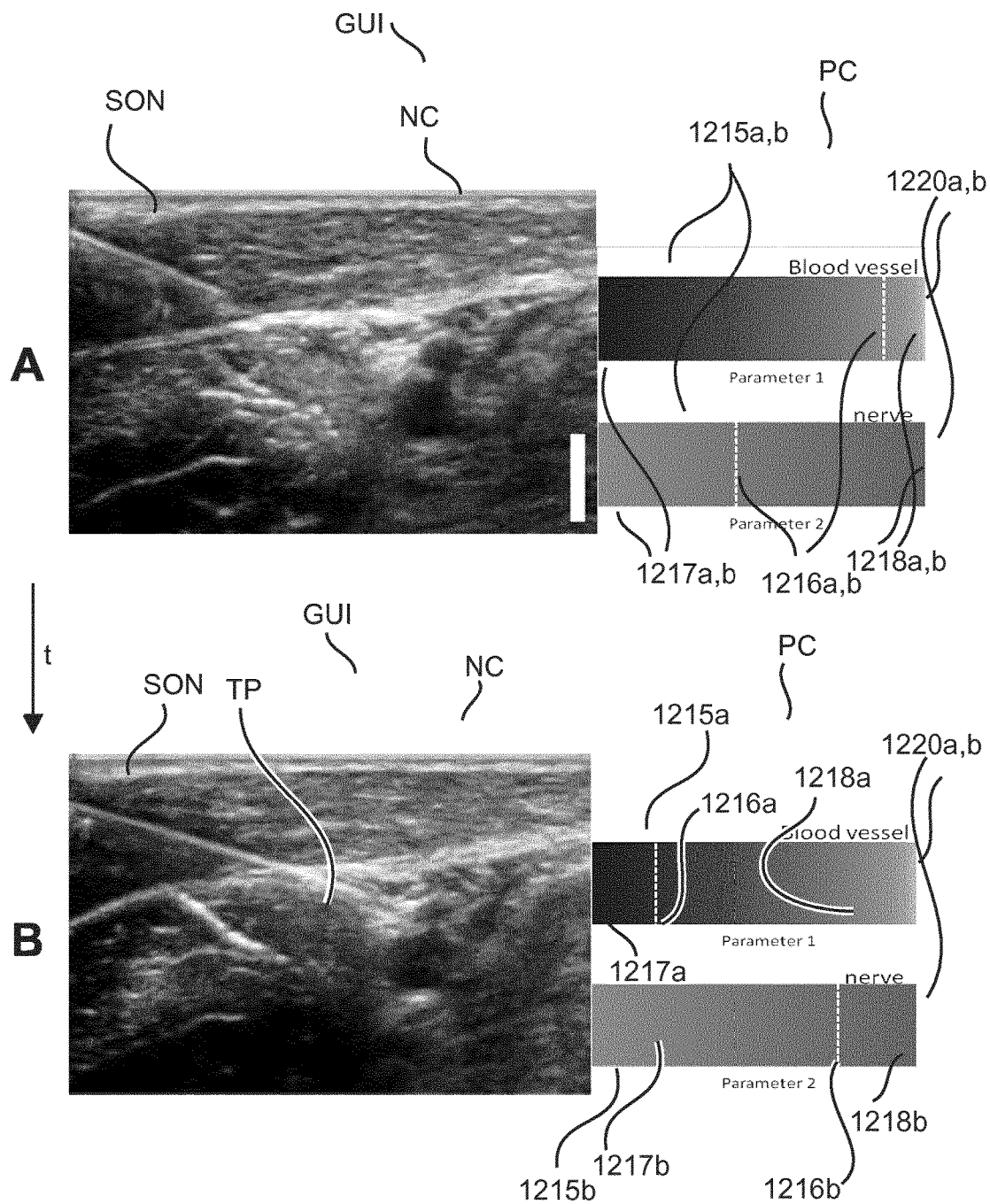
FIG. 12 shows two views different instances in time of a graphical user interface according to a second embodiment produced by the system of FIG. 10.

In the alternative embodiment as shown in FIG. 12, each transition pane or window 1220a,b (only two are now shown but this only for ease of representation) is linked to a respective transitions. Each transition pane 1120a,b includes now a respective bar or dial 1215a,b divided into two parts. For instance, the respective bar 1215,ab has two ends 1217a,b and 1218a,b each in different colors or grey values. The color or grey value transition or fuse into each other gradually as one progresses from one end 1217a.b of the bar 1215a,b to the other 1217a,b. This is schematically indicated in the Figure as a shading. The probability of being in one tissue is indicated by the intensity of color.

For instance, in one embodiment the color can be green for being nerve tissue and blue for being in non nerve tissue. In one embodiment, the more intense the hue, the higher the probability for residing in the respective tissue. For instance, dark green or grey means that the probability of being in nerve tissue is more likely, etc. The interface between the two strata however may not be necessarily in the middle of the bar 1215a,b. Each of the bar ends is associated with respective tissue type that together define the transition. The "tissue type" may also simply indicate the negation of a certain tissue type, for instance nerve tissue versus non-nerve tissue. The currently measured value of the parameter is again indicated by a respective pointer a line 1216a,b that moves in and against the backdrop of the receptive bar 1215a,b as the probe PR measures spectral properties at different positions. The further away from the dividing line into one of the two tissue types the more likely the actual tissue in front of the needle is that tissue.

FIGS. 12A,B show the user interface GUI at different instances.

In FIG. 12A, transition into a blood vessel and into a nerve is shown. As can be seen from the position of the pointer lines 1216a,b (shown as a vertical dashed line) the needle IT is most likely inside a blood vessel and likely outside nerve. In FIG. 12B, the needle IT is most likely outside a blood vessel and likely in nerve.

It is also envisaged in one embodiment to express additionally the probability in either one of the previously described embodiments in numerical form. The numbers may be shown in a tabular overlay widget (or similar) along with the graphical representation shown in FIGS. 4-8, 11-12. For example, the four transitions as per FIG. 11 could be represented numerically in the GUI as:

SubFat: 90% Muscle: 10%
Muscle: 30% NearNerve: 70%
NearNerve: 37% OnNerve: 63%
OnNerve: 55% InNerve: 45%

The numbers are purely illustrative and not limiting.

In this case, the probabilities are given independently for each transition, so that the probabilities add up to 100% for each transition. Alternatively, one could use values that sum up to less than 100% as a way to express uncertainty. Additionally, the transition that attracts the highest likelihood may be flagged up suitably such as by highlighting in a suggestive color, while unlikely transitions might be grayed out.

Although the GUI embodiments as per FIGS. 11-12 have been explained for a navigation NAV component based on live imagery (e.g., ultrasound as in FIG. 10) and the GUI embodiments as per FIGS. 4-8 have been explained for a NAV component based on a EM tracking+pre-interventional imagery, embodiments for the "converse" combinations are also envisaged herein. That is, GUI embodiments as per FIGS. 11-12 may be used with EM tracking+pre-interventional imagery and embodiments as per FIGS. 4-8 may be used instead with NAV component based on live imagery.

Also, the system may be configured to allow the user to switch between the various GUI views of FIGS. 4-8 and FIGS. 11-12 (for exploration of stratified objects), respectively.

It will be appreciated from the above, that the GUI as proposed herein affords a dynamic, real-time response common and consolidated view where spatial information is combined with exploratory information. Users are informed at one glance where they are and what type tissue they "are in". The GUIs produced by UI generator GG are dynamic in both aspects, the spatial and the exploratory. The position indicator in the NC components of the GUI and the plurality of the respective (tissue specific) pointer lines will appear to the user as moving against their respective dial elements as he or she moves about the probe PR. Also the measurement markers will appear to "pop up on the go" as user moves about the probe PR. This real-time experience is achieved by configuring the UI generator GG as an event driven module that includes a suitable event handler. The positions of the various dynamic widget elements such as pointer line and markers are re-computed many times and mapped onto their dial element. The re-computations are triggered by measurement events issued by the spectral analyzer. The events form "messages" to which the event handler is listening to in one or more channels that couple the spectral analyzers circuitry to the UI generator. Each message encodes via suitable strings or stamps information about the type of measurement that was executed and the value so measured. Intercepting those messages allows the UI generator GG the assigning the measured values to the correct pointer line in the correct pane and to compute a corresponding shift across the dial on the monitor that corresponds in proportion to the measured value. Similarly, the various color or shape-coding of information is done by suitably programmed mapper components that use interpolation schemes against defined color or grey value palettes. Similarly, spatial mappers use (for instance linear) interpolation schemes to compute the respective pointer line shifts that correspond in magnitude to the instantly measured value.

In one embodiment, the components of image processing system in particular the UI generator GG runs on a single computing system such as the workstation of the imaging modality. In an alternative embodiment an at least partly distributed architecture is likewise envisaged herein where one or more of the components are located remotely and are connected with each other in a suitable communication network.

In one embodiment, UI generator GG (or at least some its components) is arranged as a dedicated FPGA or as a hardwired (standalone) chip.

In an alternate embodiment, UI generator GG or at least some of its components are resident in a work station of the imager IM The UI generator GG or various of its components and or the data processing module of the spectral analyzer SA may be programmed in a suitable scientific computing platform such as Matlab® and may be translated into C++ or C routines suitable to run on a computing system (such as the imager's workstation). In another exemplary embodiment of the present invention, a computer program or a computer program element is provided that is characterized by being adapted to execute the method steps of the method according to one of the preceding embodiments, on an appropriate system.

Figure 14:
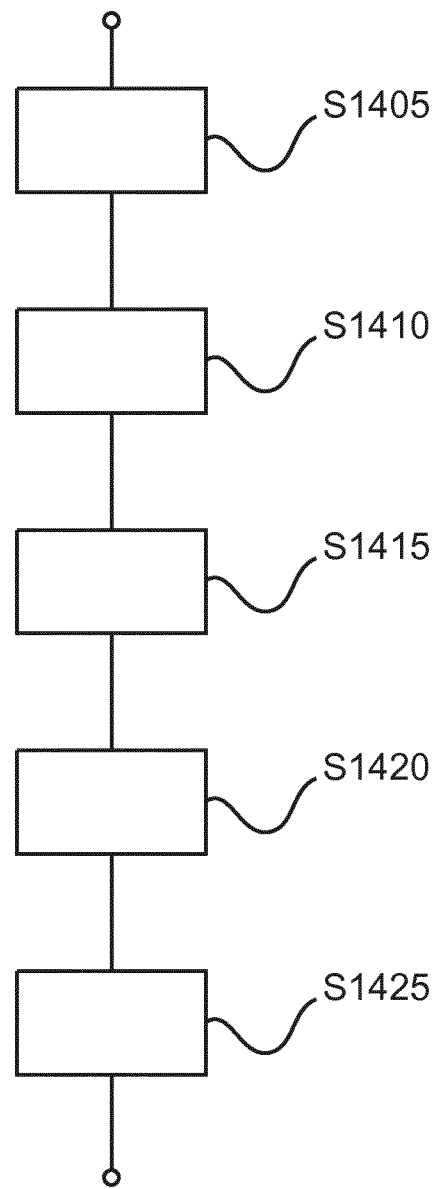
FIG. 14 shows a flow chart of a method for supporting exploring the interior of an object.

FIG. 14 is flowchart of a method for supporting exploring the interior of an object.

At step S1405 current positional information indicative of a current position of an interventional tool inside an object is received.

At step S140, non-ionizing radiation reflected off the interior of the object received.

At step S1415, the received radiation is spectrally analyzed into exploratory information about material composition and/or material type and/or tissue structure of the object's interior at or around the current position of the interventional tool.

The exploratory information comprises at least one measurement value for a material type present at or around the current tip position of the interventional tool and/or a scattering measurement value for an amount of scattering as per the received radiation;.

At step S1420 a graphics display on a display unit is produced.

At step S1425 the graphics display so produced is displayed. The graphics display includes:

i) at least one exploratory information indicator for the scatter measurement value or for the material type measurement value or for a value derived from either or both of said measurement values, the exploratory information indicator comprising a) a pointer element configured to indicate a current reading of the measurement value or a current reading of the derived value and b) a dial element configured to indicate a range of values, with the pointer element being displayed against the dial element; and ii) a position indicator for the current positional information of the tip's position in the object's interior.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

The invention claimed is:

1. A system for exploration of an interior of an object, comprising:
    an interventional tool having a tip portion for introduction into the object;
    navigation equipment configured to produce current positional information indicative of a current position of the tip inside the object whilst the tool resides in the object;
    a probe for introduction into the object, configured to receive non-ionizing radiation reflected off the interior of the object;
    a spectral analyzer configured to analyze a spectrum of the received radiation into exploratory information about material composition and/or tissue structure of the object's interior at or around the current tip position of the interventional tool, wherein the exploratory information comprises at least one measurement value for a material type present at or around the current tip position of the interventional tool and/or a scattering measurement value for an amount of scattering as per the received radiation;
    a graphical user interface generator configured to produce a graphics display on a display unit including, when displayed:
    i) at least one exploratory information indicator for the scatter measurement value or for the material type measurement value or for a value derived from either or both of said measurement values, the exploratory information indicator comprising a) a pointer element configured to indicate a current reading of at least one of the measurement value or of a current reading of the derived value and b) a dial element configured to indicate a range of values, with the pointer element being displayed against the dial element; and
    ii) a position indicator for the current positional information of the tip's position in the interior;
    and the system further comprising:
    the display unit for displaying the graphics display when the system is use.

2. The system of claim 1, wherein the spectral analyzer is configured to discriminate the material measurement value into amounts of any one of a first material type and a second material type, wherein the graphics display generated by the graphical user interface generator includes three discrete exploratory information indicators, each dedicated to the amounts of the first and second material types and the scattering value, respectively.

3. The system of claim 1, wherein the spectral analyzer is configured to discriminate the material measurement value into amounts of any one of a first material type and a second material type, wherein the spectral analyzer is configured to combine the scattering value and the measured amounts for the first and second material types into a single super value, wherein the least one exploratory information indicator is for indicating said single super value.

4. The system of claim 1, wherein the derived value is a probability value that relates to the probability of a first material type being in one of at least two states.

5. The system of claim 2, wherein the measurement value relates to the amount of the first or second material currently present at or around the tip of the interventional tool.

6. The system of claim 1, wherein the exploratory information indicator includes a graphical indication for two probability densities, one probability density describing a distribution of the measurement value for a first material type and the other probability density describing the distribution of the measured value for a second material type, the exploratory information indicator thereby supporting exploring transitions of strata of the first and second material types within the object, wherein the graphical indication of the two probability densities is by curve representation or by color-coding.

7. The system of claim 1, wherein the navigation equipment is an electromagnetic tracking device with a sensor attached to the interventional tool to relate to the tip position to electromagnetic field strength sensed by the sensor and wherein the position indicator is a graphical symbol superimposed on imagery of the object's interior or wherein the navigation equipment is a fluoroscopy imaging device or a ultrasound imaging device or X-ray or CT or MRI or PET-CT and wherein the positional indicator is defined by a footprint of the tip of the interventional tool in a current fluorogram or in a current ultrasound image, respectively.

8. The system of claim 3, wherein the first or second material types is hemoglobin or water and the respective measurement value relates to a respective concentration of hemoglobin or water.

9. The system of claim 8, wherein the dial element is graduated and/or color- or grey-value coded.

10. The system of claim 9, wherein a position of the pointer relative to dial changes responsive to a change of position of the interventional tool within the object.

11. The system of claim 1, wherein the tool comprises an endoscope and/or a catheter and/or a biopsy needle and or a forceps biopsy tool and/or a brush biopsy tool and/or a needle for fluid injection into the object.

12. The system of claim 1, wherein, responsive to the spectral analyzer's analyzing the received radiation into a current material type measurement value or into the scatter measurement value, the graphical user interface generator operates to include in the graphics display one or more measurement markers whose position in the graphics display corresponds to the current positional information, wherein the one or more measurement markers are color- and/or grey-value and/or shape coded according to the current material type measurement value or the scatter measurement value.

13. The system of claim 1, where the probe further comprises an optical waveguides.

14. The system of claim 13, wherein the optical waveguide comprises an optical fiber.

15. The system of claim 1, further comprising an optical source configured to provide light to the probe, and an optical sensor configured to receive reflected light reflected by the object.

16. The system of claim 15, wherein diffuse reflectance (DRS) and fluorescence measurements are provided by the optical source and optical sensor.

17. A method comprising the steps of:
    receiving current positional information indicative of a current position of an interventional tool inside an object;
    receiving, by a probe, non-ionizing radiation reflected off an interior of the object;

spectrally analyzing, by a spectral analyzer, the received radiation into exploratory information about material composition and/or type and/or tissue structure of the object's interior at or around the current position of the interventional tool, the exploratory information comprising at least one measurement value for a material type present at or around the current position of the interventional tool and/or a scattering measurement value for an amount of scattering as per the received radiation;

producing, by a graphical user interface generator, a graphics display for display on a display unit, displaying the graphics display on the display unit, wherein the graphics display includes:

i) at least one exploratory information indicator for the scatter measurement value or for the material type measurement value or for a value derived from either or both of said measurement values, the exploratory information indicator comprising a) a pointer element configured to indicate a current reading of the measurement value or a current reading of the derived value and b) a dial element configured to indicate a range of values, with the pointer element being displayed against the dial element; and ii) a position indicator for the current positional information of the position in the interior.

18. A non-transitory computer readable medium that stores instructions, which, when being executed by one or more processing units, is adapted to perform a method, comprising:

receiving current positional information indicative of a current position of an interventional tool inside an object;

receiving, by a probe, non-ionizing radiation reflected off an interior of the object;

spectrally analyzing, by a spectral analyzer, the radiation received by the probe into exploratory information about material composition and/or type and/or tissue structure of the object's interior at or around the current position of the interventional tool, the exploratory information comprising at least one measurement value for a material type present at or around the current position of the interventional tool and/or a scattering measurement value for an amount of scattering as per the radiation received by the probe;

producing, by a graphical user interface generator, a graphics display for display on a display unit, wherein the graphics display includes:

i) at least one exploratory information indicator for the scatter measurement value or for the material type measurement value or for a value derived from either or both of said measurement values, the exploratory information indicator comprising a) a pointer element configured to indicate a current reading of the measurement value or a current reading of the derived value and b) a dial element configured to indicate a range of values, with the pointer element being displayed against the dial element; and ii) a position indicator for the current positional information of the current position of the interventional tool in the interior.

* * * * *